US008066742B2

(12) United States Patent
Anderson et al.

(10) Patent No.: US 8,066,742 B2
(45) Date of Patent: Nov. 29, 2011

(54) INTERVERTEBRAL PROSTHETIC DEVICE FOR SPINAL STABILIZATION AND METHOD OF IMPLANTING SAME

(75) Inventors: Kent M. Anderson, San Jose, CA (US); Eric C. Lange, Pleasanton, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 92 days.

(21) Appl. No.: 11/095,215

(22) Filed: Mar. 31, 2005

(65) Prior Publication Data
US 2006/0224159 A1    Oct. 5, 2006

(51) Int. Cl.
A61B 17/70    (2006.01)
(52) U.S. Cl. .................................. 606/249; 606/279
(58) Field of Classification Search .... 623/17.11–17.16;
606/246–249
See application file for complete search history.

(56) References Cited

U.S. PATENT DOCUMENTS

| | | | |
|---|---|---|---|
| 2,677,369 A * | 5/1954 | Knowles | 606/249 |
| 3,397,699 A | 8/1968 | Kohl | |
| 3,648,691 A | 3/1972 | Lumb et al. | |
| 4,011,602 A | 3/1977 | Rybicki et al. | |
| 4,257,409 A | 3/1981 | Bacal et al. | |
| 4,327,736 A | 5/1982 | Inoue | |
| 4,554,914 A | 11/1985 | Kapp et al. | |
| 4,573,454 A | 3/1986 | Hoffman | |
| 4,604,995 A | 8/1986 | Stephens et al. | |
| 4,611,582 A * | 9/1986 | Duff | 606/61 |
| 4,686,970 A | 8/1987 | Dove et al. | |
| 4,721,103 A | 1/1988 | Freedland | |
| 4,827,918 A | 5/1989 | Olerud | |
| 5,000,165 A | 3/1991 | Watanabe | |
| 5,011,484 A * | 4/1991 | Breard | 606/249 |
| 5,047,055 A | 9/1991 | Bao et al. | |
| 5,092,866 A | 3/1992 | Breard et al. | |
| 5,133,717 A | 7/1992 | Chopin | |
| 5,201,734 A | 4/1993 | Cozad et al. | |
| 5,267,999 A * | 12/1993 | Olerud | 606/277 |
| 5,306,275 A | 4/1994 | Bryan | |
| 5,306,308 A | 4/1994 | Gross et al. | |
| 5,316,422 A | 5/1994 | Coffman | |
| 5,360,430 A | 11/1994 | Lin | |
| 5,366,455 A | 11/1994 | Dove | |
| 5,415,659 A | 5/1995 | Lee et al. | |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |

(Continued)

FOREIGN PATENT DOCUMENTS
DE    2821678 A1    11/1979
(Continued)

OTHER PUBLICATIONS

U.S. Appl. No. 11/095,214, filed Mar. 31, 2005, Anderson.
(Continued)

*Primary Examiner* — Eduardo C Robert
*Assistant Examiner* — Steven J Controneo

(57) ABSTRACT

An intervertebral prosthetic device for spinal stabilization and a method of using same according to which a body member is implanted between two adjacent vertebrae so that a spinous processes of a vertebrae extends into a notch formed in the body member. A groove is also formed in the body member that engages one of the vertebrae.

19 Claims, 3 Drawing Sheets

U.S. PATENT DOCUMENTS

| | | | |
|---|---|---|---|
| 5,527,314 A * | 6/1996 | Brumfield et al. | 606/61 |
| 5,609,634 A | 3/1997 | Voydeville | |
| 5,628,756 A | 5/1997 | Barker, Jr. et al. | |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,755,798 A | 5/1998 | Papavero et al. | |
| 5,800,547 A | 9/1998 | Schafer et al. | |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,059,829 A | 5/2000 | Schlapfer et al. | |
| 6,068,630 A | 5/2000 | Zucherman et al. | |
| 6,074,390 A | 6/2000 | Zucherman et al. | |
| 6,113,638 A | 9/2000 | Williams et al. | |
| 6,132,464 A | 10/2000 | Martin | |
| 6,143,031 A | 11/2000 | Knothe et al. | |
| 6,143,032 A | 11/2000 | Schafer et al. | |
| 6,143,033 A | 11/2000 | Paul et al. | |
| 6,179,873 B1 | 1/2001 | Zientek | |
| 6,214,037 B1 | 4/2001 | Mitchell et al. | |
| 6,224,631 B1 | 5/2001 | Kohrs | |
| 6,277,149 B1 | 8/2001 | Boyle et al. | |
| 6,293,949 B1 | 9/2001 | Justis et al. | |
| 6,325,827 B1 | 12/2001 | Lin | |
| 6,352,537 B1 | 3/2002 | Strnad | |
| 6,364,883 B1 | 4/2002 | Santilli | |
| 6,383,221 B1 | 5/2002 | Scarborough et al. | |
| 6,402,750 B1 | 6/2002 | Atkinson et al. | |
| 6,419,703 B1 | 7/2002 | Fallin et al. | |
| 6,440,169 B1 | 8/2002 | Elberg et al. | |
| 6,451,019 B1 | 9/2002 | Zucherman et al. | |
| 6,500,178 B2 | 12/2002 | Zucherman et al. | |
| 6,503,279 B1 | 1/2003 | Webb et al. | |
| 6,514,256 B2 | 2/2003 | Zucherman et al. | |
| 6,520,990 B1 | 2/2003 | Ray | |
| 6,530,955 B2 | 3/2003 | Boyle et al. | |
| 6,547,823 B2 | 4/2003 | Scarborough et al. | |
| 6,565,605 B2 * | 5/2003 | Goble et al. | 623/17.11 |
| 6,582,433 B2 | 6/2003 | Yun | |
| 6,613,090 B2 | 9/2003 | Fuss et al. | |
| 6,626,944 B1 * | 9/2003 | Taylor | 623/17.16 |
| 6,645,207 B2 | 11/2003 | Dixon et al. | |
| 6,669,729 B2 | 12/2003 | Chin | |
| 6,695,842 B2 | 2/2004 | Zucherman et al. | |
| 6,699,246 B2 | 3/2004 | Zucherman et al. | |
| 6,706,067 B2 | 3/2004 | Shimp et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,843,805 B2 | 1/2005 | Webb et al. | |
| 6,902,580 B2 | 6/2005 | Fallin et al. | |
| 6,946,000 B2 | 9/2005 | Senegas et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,097,654 B1 | 8/2006 | Freedland | |
| 7,101,375 B2 | 9/2006 | Zucherman et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,377,942 B2 | 5/2008 | Berry | |
| 7,442,208 B2 | 10/2008 | Mathieu et al. | |
| 7,445,637 B2 | 11/2008 | Taylor | |
| 7,604,652 B2 | 10/2009 | Arnin et al. | |
| 7,658,752 B2 | 2/2010 | Labrom et al. | |
| 7,749,252 B2 | 7/2010 | Zucherman et al. | |
| 7,771,456 B2 | 8/2010 | Hartmann et al. | |
| 7,901,430 B2 | 3/2011 | Matsuura et al. | |
| 2001/0016743 A1 | 8/2001 | Zucherman et al. | |
| 2002/0143331 A1 | 10/2002 | Zucherman et al. | |
| 2003/0040746 A1 | 2/2003 | Mitchell et al. | |
| 2003/0045940 A1 | 3/2003 | Eberlein et al. | |
| 2003/0065330 A1 | 4/2003 | Zucherman et al. | |
| 2003/0153915 A1 | 8/2003 | Nekozuka et al. | |
| 2004/0097931 A1 | 5/2004 | Mitchell | |
| 2004/0106995 A1 | 6/2004 | Le Couedic et al. | |
| 2004/0117017 A1 | 6/2004 | Pasquet et al. | |
| 2004/0133280 A1 | 7/2004 | Trieu | |
| 2004/0199255 A1 | 10/2004 | Mathieu et al. | |
| 2005/0010293 A1 | 1/2005 | Zucherman et al. | |
| 2005/0033434 A1 | 2/2005 | Berry | |
| 2005/0049708 A1 | 3/2005 | Atkinson et al. | |
| 2005/0165398 A1 | 7/2005 | Reiley | |
| 2005/0203512 A1 * | 9/2005 | Hawkins et al. | 606/61 |
| 2005/0203624 A1 | 9/2005 | Serhan et al. | |
| 2005/0228391 A1 | 10/2005 | Levy et al. | |
| 2005/0245929 A1 | 11/2005 | Winslow et al. | |
| 2005/0261768 A1 * | 11/2005 | Trieu | 623/17.11 |
| 2005/0267579 A1 | 12/2005 | Reiley et al. | |
| 2005/0288672 A1 | 12/2005 | Feree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0129239 A1 | 6/2006 | Kwak | |
| 2006/0136060 A1 | 6/2006 | Taylor | |
| 2006/0149242 A1 | 7/2006 | Kraus et al. | |
| 2006/0182515 A1 | 8/2006 | Panasik et al. | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 | 10/2006 | Anderson | |
| 2006/0235387 A1 | 10/2006 | Peterman | |
| 2006/0235532 A1 | 10/2006 | Meunier et al. | |
| 2006/0241601 A1 | 10/2006 | Trautwein et al. | |
| 2006/0241613 A1 | 10/2006 | Brueneau et al. | |
| 2006/0241757 A1 | 10/2006 | Anderson | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 * | 11/2006 | Petrini et al. | 606/61 |
| 2006/0271049 A1 | 11/2006 | Zucherman et al. | |
| 2006/0282075 A1 | 12/2006 | Labrom et al. | |
| 2006/0282079 A1 | 12/2006 | Labrom et al. | |
| 2006/0293662 A1 | 12/2006 | Boyer, II et al. | |
| 2006/0293663 A1 | 12/2006 | Walkenhorst et al. | |
| 2007/0005064 A1 | 1/2007 | Anderson et al. | |
| 2007/0010813 A1 | 1/2007 | Zucherman et al. | |
| 2007/0043362 A1 | 2/2007 | Malandain et al. | |
| 2007/0043363 A1 | 2/2007 | Malandain et al. | |
| 2007/0100340 A1 | 5/2007 | Lange et al. | |
| 2007/0123861 A1 | 5/2007 | Dewey et al. | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0198091 A1 | 8/2007 | Boyer et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |

| | | | |
|---|---|---|---|
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0140082 A1 | 6/2008 | Erdem et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0195152 A1 | 8/2008 | Altarac et al. |
| 2008/0215094 A1 | 9/2008 | Taylor |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0240283 A1 | 9/2009 | Carls et al. |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| EP | 1138268 | 10/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| FR | 2858929 | 2/2005 |
| FR | 2884135 A1 | 4/2005 |
| JP | 02-224660 | 9/1990 |
| JP | 09-075381 | 3/1997 |
| JP | 2003-079649 | 3/2003 |
| SU | 988281 | 1/1983 |
| SU | 1484348 A1 | 6/1989 |
| SU | 1484348 | 7/1989 |
| WO | WO 94/26192 | 11/1994 |
| WO | WO 94/26195 | 11/1994 |
| WO | WO 98/20939 | 5/1998 |
| WO | WO 02/051326 | 7/2002 |
| WO | 03/015645 | 2/2003 |
| WO | WO 2004/047691 A1 | 6/2004 |
| WO | 2004/084743 A1 | 10/2004 |
| WO | WO 2004/084743 * | 10/2004 |
| WO | 2005/009300 | 2/2005 |
| WO | WO 2005/009300 A1 | 2/2005 |
| WO | WO 2005/044118 A1 | 5/2005 |
| WO | WO 2005/110258 A1 | 11/2005 |
| WO | 2005/115261 | 12/2005 |
| WO | WO 2006/064356 A1 | 6/2006 |
| WO | WO 2006/110578 A2 | 10/2006 |
| WO | 2007/001994 | 1/2007 |
| WO | WO 2007/034516 A1 | 3/2007 |
| WO | WO2007052975 A | 5/2007 |

OTHER PUBLICATIONS

European Patent Office, International Searching Authority, Notification of Transmittal of the International Search Report and the Written Opinion of the International Searching Authority or the Declaration, International Application No. PCT/US2007/062405, Aug. 2, 2007, 9 pages.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," Spine, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les instabilites," Maîtrise Orthopédique, Jul. 1993, pp. 18, No. 25.
Garner et al., "Development and Preclinical Testing of a New Tension-Band Device for the Spine: The Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Annmortizzante," S.O.T.I.M.I. Societé di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfó, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodése," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiese!, ed., Jun. 1994, pp. 116-123, vol. 6, No. 2.

Wittenberg et al., "Flexibility and Distraction after Monosegmental and Bisegmental Lumbrosacral Fixation with Angular Stable Fixators," Spine, 1995, pp. 1227-1232, vol. 20, No. 11.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "DIAM Device for Low Back Pain In Degenerative Disc Disease 24 Months Follow-up," Advances in Minimally Invasive Surgery And Therapy for Spine and Nerves, Alexandre et al., eds., 2011, pp. 177-182, Spinger-Verlat/Wien.

Phillips et al., "Biomechanics of Posterior Dynamic Stabilizing Device (DIAM) After Facetectomy and Discectemy," The Spine Journal, 2006, vol. 6, pp. 714-722.

Taylor et al., "Device For Intervertebral Assisted Motion: Technique and Initial Results," Neurosurg. Focus, Jan. 2007, vol. 22, No. 1, pp, 1-6.

Wilke et al., "Biomechanical Effect of Different Lumbar Interspinous Implants on Flexibility and Intradiscal Pressure," Eur. Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, 123(21), pp. 2974-2977.

* cited by examiner

INTERVERTEBRAL PROSTHETIC DEVICE FOR SPINAL STABILIZATION AND METHOD OF IMPLANTING SAME

BACKGROUND

The present invention relates to an intervertebral prosthetic device for stabilizing the human spine, and a method of implanting same.

Spinal discs that extend between adjacent vertebrae in vertebral columns of the human body provide critical support between the adjacent vertebrae. These discs can rupture, degenerate, and/or protrude by injury, degradation, disease, or the like, to such a degree that the intervertebral space between adjacent vertebrae collapses as the disc loses at least a part of its support function, which can cause impingement of the nerve roots and severe pain.

In these cases, intervertebral prosthetic devices have been designed that can be implanted between the adjacent vertebrae, both anterior and posterior of the column, to prevent the collapse of the intervertebral space between the adjacent vertebrae and thus stabilize the spine.

However, many of these devices have less than optimum biomechanics, are relatively difficult to insert, have insufficient strength, and often do not provide an optimum fit with the anatomy.

SUMMARY

Therefore, the intervertebral prosthetic device according to an embodiment of the invention overcomes the above deficiencies by providing improved biomechanics and increased strength, in addition to being relatively easy to insert, yet provides an improved fit with the anatomy.

Various embodiments of the invention may possess one or more of the above features and advantages, or provide one or more solutions to the above problems existing in the prior art.

DETAILED DESCRIPTION

Figure 1:
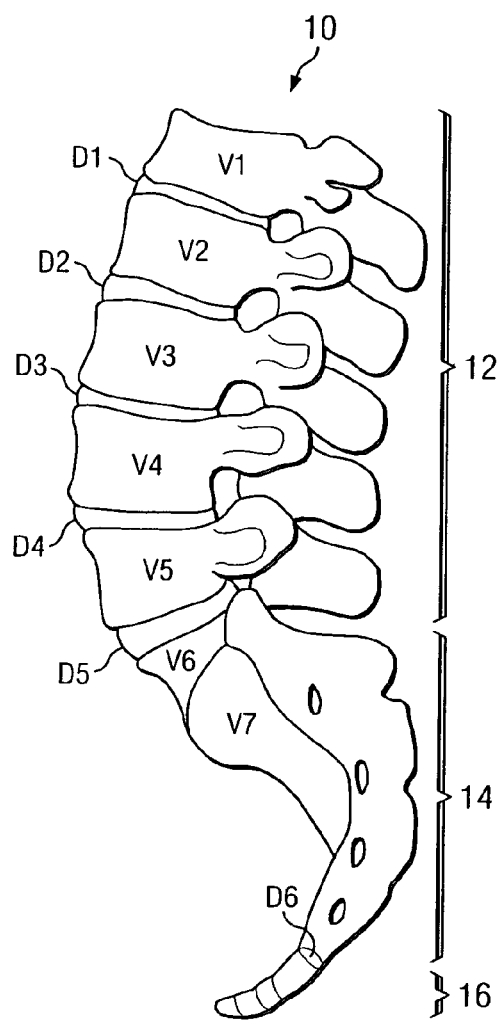
FIG. 1 is a side elevational view of an adult human vertebral column.
Figure 2:
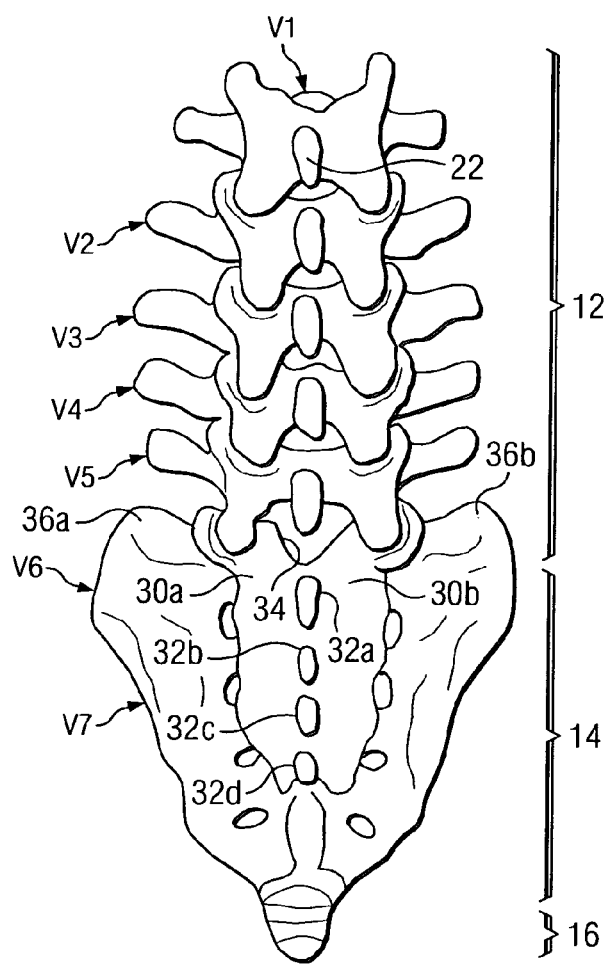
FIG. 2 is a posterior elevational view of the column of FIG. 1.

With reference to FIGS. 1 and 2, the reference numeral 10 refers, in general, to a human vertebral column 10. The lower portion of the vertebral column 10 is shown and includes the lumbar region 12, the vertebrae V6, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The vertebrae V6 includes five fused vertebrae, one of which is a superior vertebrae V6 separated from the vertebrae V5 by a disc D5. The other four fused vertebrae of the sacrum 14 are referred to collectively as V7. A disc D6 separates the vertebrae V6 from the coccyx 16 which includes four fused vertebrae (not referenced).

Figure 3:
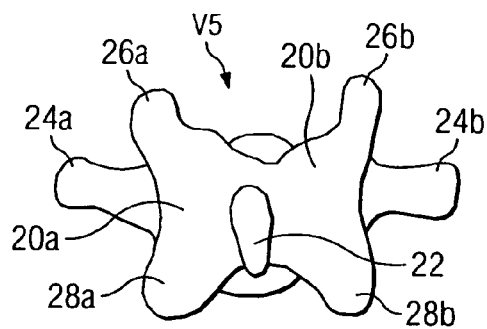
FIG. 3 is an enlarged, front elevational view of one of the vertebrae of the column of FIGS. 1 and 2.

With reference to FIG. 3, the vertebrae V5 includes two laminae 20a and 20b extending to either side (as viewed in FIG. 2) of a spinous process 22 that extends posteriorly from the juncture of the two laminae. Two transverse processes 24a and 24b extend laterally from the laminae 20a and 20b, respectively. Two articular processes 26a and 26b extend superiorly from the laminae 20a and 20b, respectively, and two articular processes 28a and 28b extend inferiorly from the laminae 20a and 20b, respectively. The inferior articular processes 28a and 28b rest in the superior articular process of the vertebra V2 to form a facet joint. Since the other vertebrae V1-V4 are similar to the vertebrae V5, they will not be described in detail.

Referring again to FIG. 2, the vertebrae V6 of the sacrum 14 includes two laminae 30a and 30b extending to either side (as viewed in FIG. 2) of a median sacral crest, or spinous process, 32a that extends inferiorly from a ridge 34 and posteriorly from the juncture of the two laminae. The vertebrae V6 also includes a pair of sacral wings 36a and 36b that extend laterally from the laminae 30a and 30b, respectively. Four additional axially-spaced sacral crests, or spinous processes, 32b-32d are associated with the fused vertebrae V7 of the sacrum 14 and extend inferiorly from the spinous process 32a.

Figure 4:
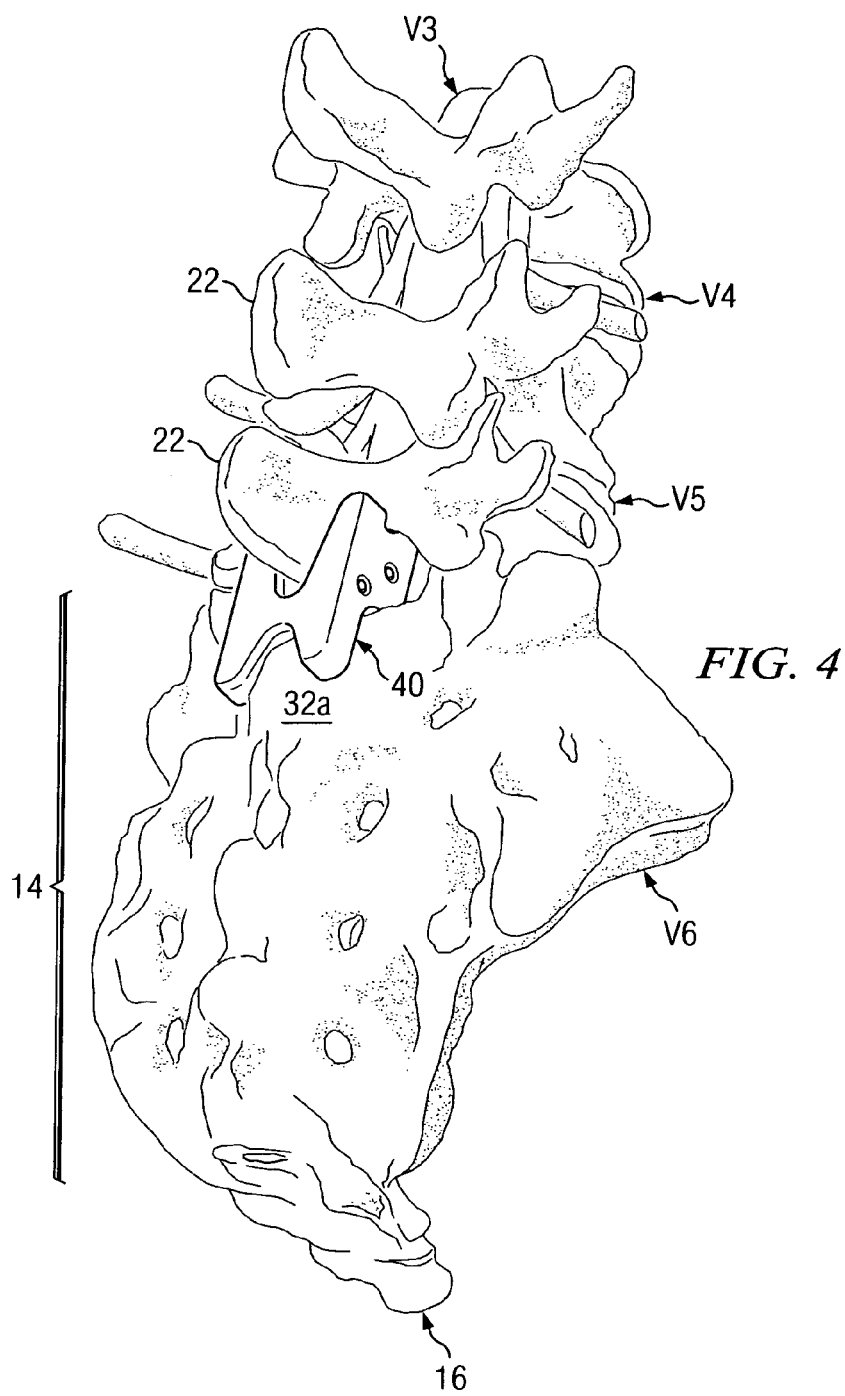
FIG. 4 is an enlarged, partial, isometric view of a portion of the column of FIGS. 1 and 2, including the lower three vertebrae of the column, and depicting an intervertebral prosthetic device according to an embodiment of the invention inserted between two adjacent vertebrae.

Referring to FIG. 4, it will be assumed that, for one or more of the reasons set forth above, the vertebrae V5 and V6 are not being adequately supported by the disc D4 and that it is therefore necessary to provide supplemental support and stabilization of these vertebrae. To this end, an intervertebral disc prosthetic device 40 according to an embodiment of the invention is implanted between the spinous processes 22 of the vertebrae V5 and the crest, or spinous process 32a, of the vertebrae V6.

Figure 5:
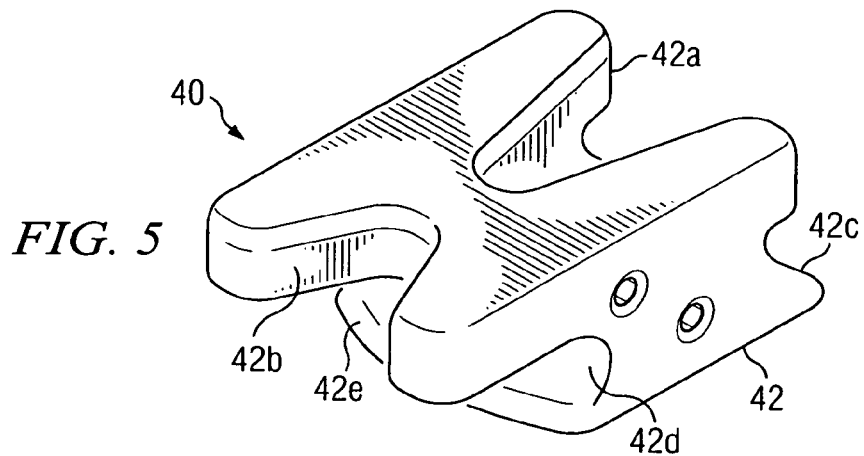
FIG. 5 is an enlarged, isometric, view of the prosthetic device of FIG. 3.
Figure 6:
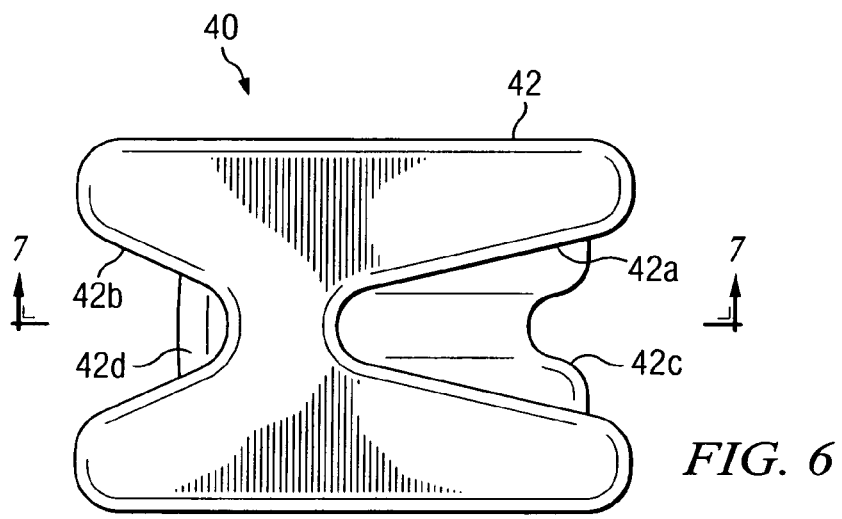
FIG. 6 is an enlarged, top plan view of the prosthetic device of FIG. 5.
Figure 7:
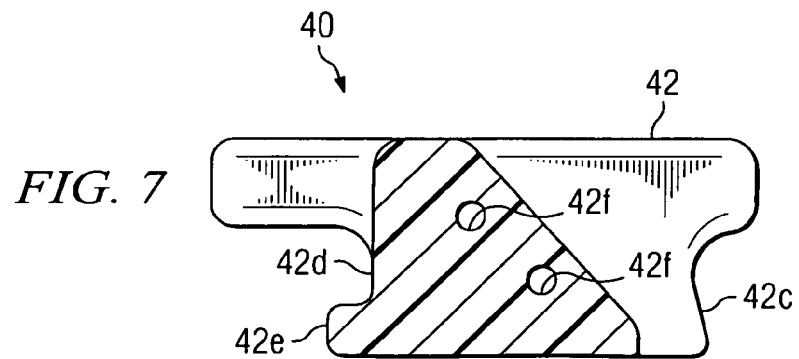
FIGS. 7 is a cross-sectional view taken along the line 7-7 of FIG. 6.

The device is shown in detail in FIGS. 5-7 and includes a solid body member 42 having a generally rectangular cross section in each plane with the exception of several notches and cuts to be described.

In particular, two curved grooves, or notches, 42a and 42b are formed in the upper portions of the respective end portions of the body member, as viewed in the drawings. A laterally extending angled cut, or groove 42c, having a curved cross section, is formed in the underside of the body member 42 below the notch 42a, as viewed in FIG. 5 and 7. Similarly, a laterally extending cut, or groove 42d, also having a curved cross section, is formed in the underside of the body member 42 below the notch 42b. The shape of the cut 42d is such that a tab, or hook, 42e (FIG. 7) is defined on the underside of the body member.

Two laterally extending, through openings 42f are formed through the body member 42 for receiving cables, or the like, to tether the device to the vertebrae V5 and V6 when the device 40 is implanted between the vertebrae V5 and V6 in the position shown in FIG. 4.

Referring to FIG. 4, the device 40 is inserted between the vertebrae V5 and the vertebrae V6 with the spinous process 22 of the vertebrae V5 extending in the notch 42a of the body member 42, and the crest, or spinous process, 32a of the vertebrae V6 extending in the notch 42b of the body member. The groove 42c (FIGS. 5 and 7) thus extends superiorly and extends around the corresponding edges of the laminae 30a and 30b (FIG. 2) of the vertebrae V5, and the groove 42d extends inferiorly and fits around the ridge 34 (FIG. 2) of the vertebrae V6, with the tab 42e extending under the latter ridge.

It is understood that the body member 42 can be fabricated from any conventional material or combination of materials. For example, it could have an inner core of a relatively hard material, such as hard rubber or plastic, which is surrounded by a relatively soft material such as silicone, which can be molded around the core.

The device 40 is relatively easy to insert between the vertebrae V5 and V6 in the manner described above, and readily fits the vertebrae. The grooves 42c and 42d, as well as the tab 42e, aid in retaining the device 40 in the implanted position, and the core 42f adds strength to the device 40, while the soft material surrounding the core minimizes damage to the processes 22 and 30a of the vertebrae V5 and V6, respectively.

Variations

It is understood that variations may be made in the foregoing without departing from the invention and examples of some variations are as follows:

Any conventional substance that promotes bone growth, such as HA coating, BMP, or the like, can be incorporated in the body member 42;

The body member 42 may have through holes formed therein to improve integration of the bone growth;

The body member 42 may vary in shape, size, composition, and physical properties;

The number and location of the notches and grooves formed in the body member 42 can vary;

The prosthetic device 40 can be placed between two vertebrae in the vertebral column 10 other than the ones described above;

The body member 42 can be fabricated from materials other than those described above;

Bilateral extrusions, or the like, can be provided on the body member 42 to enable a tethering device to be attached to the component;

The prosthetic device 40 can be implanted between body portions other than vertebrae;

The prosthetic device 40 can be inserted between two vertebrae following a discectomy in which a disc between the adjacent vertebrae is removed, or corpectomy in which at least one vertebrae is removed;

The spatial references made above, such as "under", "over", "between", "flexible, soft", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art, or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A method of implanting a prosthetic device comprising:
inserting a single-piece spacer between a superior vertebra and an adjacent inferior vertebra; the spacer having a center and comprising:
a posterior portion comprising:
first and second spinous-process receiving notches;
first, second, third, and fourth flanges; the first and second flanges forming the first notch; the third and fourth flanges forming the second notch oriented generally opposite the first notch;
an intermediate section abutting the first, second, third, and fourth flanges; the intermediate section separating the first notch from the second notch;
the intermediate section having a posterior face that is flush with both a posterior face of the first flange and a posterior face of the second flange;
an anterior portion having a fifth flange forming a groove with the first flange, the groove forming an upwardly facing concave surface;
the first notch and groove each having respective minimum points;
wherein the spacer is monolithically formed;
receiving a spinous process of the superior vertebra in the first notch and receiving a portion of the inferior vertebra in the second notch such that the first and second notches extend through a sagittal plane defined by the superior and inferior vertebrae;
wherein, after the receiving step and when the spacer is viewed normal to the sagittal plane, the minimum point of the groove is disposed along an upper perimeter profile of the spacer at a point closest to the center of the spacer and the minimum point of the groove is positioned vertically above the minimum point of the first notch;
wherein the anterior portion is disposed more anteriorly than the posterior portion.

2. The method of claim 1 wherein the portion of the inferior vertebra received in the second notch is a portion of a sacrum.

3. The method of claim 2 wherein the portion of the inferior vertebra received in the second notch is a median sacral crest.

4. The method of claim 1 wherein the fifth flange is shorter than the third and fourth flanges.

5. The method of claim 1 wherein the fifth flange includes an indentation and wherein when the spacer is disposed between the superior vertebra and the adjacent inferior vertebra:
the indentation forms an upwardly facing concave surface having a minimum point;
the minimum points of the first notch and the indentation are disposed in the sagittal plane with the minimum point of the first notch being vertically offset from the minimum point of the indentation along the sagittal plane.

6. An prosthetic device for insertion between first and second vertebrae, the device comprising:
a single-piece body having an posterior portion and an anterior portion;
the posterior portion comprising:
first and second spinous-process receiving notches;
first, second, third, and fourth flanges; the first and second flanges forming the first notch; the third and fourth flanges forming the second notch;

an intermediate section abutting the first, second, third, and fourth flanges;
the intermediate section separating the first notch from the second notch; the intermediate section having a posterior face that is flush with both a posterior face of the first flange and a posterior face of the second flange;
the anterior portion having a fifth flange forming a first groove with the first flange, the first groove forming an upwardly facing concave surface;
the anterior portion having a sixth flange forming a second groove with the third and fourth flanges
the first notch and first groove each having respective minimum points;
wherein the body is monolithically formed;
wherein the body is configured such that when the body is inserted directly between the first and second vertebrae:
the first notch forms a superiorly facing concave surface and extends through a sagittal plane defined by the first and second vertebrae;
the second notch forms an inferiorly facing concave surface and extends through the sagittal plane;
the second groove opens inferiorly, extends laterally, and is disposed more anteriorly than the first and second notches;
wherein the body is configured such that when the body is inserted between the first and second vertebrae and viewed normal to the sagittal plane, the minimum point of the first groove is disposed along an upper perimeter profile of the body at a point closest to the center of the body and the minimum point of the first groove is positioned vertically above the minimum point of the first notch.

7. The device of claim 6 wherein the anterior portion includes a substantially planar anterior face.

8. The device of claim 6 wherein the second notch and the second groove are generally perpendicular with respect to each other.

9. The device of claim 6 wherein the first notch is longer than the second notch.

10. The device of claim 6 wherein the second groove is shaped to extend around corresponding edges of the lamina of one of the first and second vertebrae.

11. The device of claim 6 wherein the second groove is shallower than the second notch and shaped to extend around a superior edge of the lamina of one of the first and second vertebrae.

12. The device of claim 6 wherein the first and second grooves are generally parallel.

13. The device of claim 6 wherein the body further comprises first and second conduits extending through the body member for engaging respective tethers for attaching the body member to at least one of the vertebrae, the conduits extending generally parallel to the first and second grooves.

14. The device of claim 6 wherein the posterior face of the intermediate section is flush with a posterior face of the third flange and a posterior face of the fourth flange.

15. The device of claim 6 wherein the fifth flange is shorter than the third and fourth flanges.

16. The device of claim 6 wherein the fifth flange includes an indentation and wherein when the body is disposed between the first and second vertebrae:
the indentation forms an upwardly facing concave surface having a minimum point;
the minimum points of the first notch and the indentation are disposed in the sagittal plane with the minimum point of the first notch being vertically offset from the minimum point of the indentation along the sagittal plane.

17. A method of implanting a prosthetic device comprising:
inserting a single-piece spacer between a superior vertebra and an adjacent inferior vertebra; the spacer comprising:
a posterior portion comprising:
first and second spinous-process receiving notches;
first, second, third, and fourth flanges; the first and second flanges forming the first notch; the third and fourth flanges forming the second notch oriented generally opposite the first notch;
a substantially planar posterior face;
an intermediate section on the posterior face abutting the first, second, third, and fourth flanges; the intermediate section separating the first notch from the second notch; the intermediate section not extending more posteriorly than the first and second flanges;
an anterior portion having a fifth flange forming a first groove with the first flange, the first groove forming an upwardly facing concave surface;
the anterior portion having a sixth flange forming a second groove with the third and forth flanges;
the first notch and first groove each having respective minimum points;
wherein the spacer is monolithically formed;
receiving a spinous process of the superior vertebra in the first notch and receiving a portion of the inferior vertebra in the second notch such that the first and second notches extend through a sagittal plane defined by the superior and inferior vertebrae;
receiving a portion of a ridge of the inferior vertebra into the second groove;
wherein the anterior portion is disposed more anteriorly than the posterior portion;
wherein after the receiving steps and when the spacer is viewed normal to the sagittal plane, the minimum point of the first groove is disposed along an upper perimeter profile of the spacer at a point closest to the center of the spacer and the minimum point of the first groove is positioned vertically above the minimum point of the first notch.

18. The method of claim 17 wherein the fifth flange is shorter than the third and fourth flanges.

19. The method of claim 17 wherein the fifth flange includes an indentation and wherein when the spacer is disposed between the superior vertebra and the adjacent inferior vertebra:
the indentation forms an upwardly facing concave surface having a minimum point;
the minimum points of the first notch and the indentation are disposed in the sagittal plane with the minimum point of the first notch being vertically offset from the minimum point of the indentation along the sagittal plane.

* * * * *